United States Patent
Rosales et al.

(10) Patent No.: US 7,150,890 B2
(45) Date of Patent: Dec. 19, 2006

(54) PROCESS FOR THE PURIFICATION OF MARIGOLD XANTHOPHYLLS

(76) Inventors: Jose Antonio Socla Rosales, Choquehuanca 845, Lima 27 (PE); M. C. Mario D. Torres Cardona, Lago Zurich No. 6708, Col., Lagos del Bosque, Monterrey, N.L. 64890 (MX)

( * ) Notice: Subject to any disclaimer, the term of this patent is extended or adjusted under 35 U.S.C. 154(b) by 297 days.

(21) Appl. No.: 10/948,088

(22) Filed: Sep. 22, 2004

(65) Prior Publication Data
US 2005/0153002 A1  Jul. 14, 2005

(30) Foreign Application Priority Data
Sep. 22, 2003  (PE) .................................... 000966

(51) Int. Cl.
*A61K 36/00* (2006.01)
(52) U.S. Cl. .................... 424/778; 424/725
(58) Field of Classification Search ............ None
See application file for complete search history.

(56) References Cited

U.S. PATENT DOCUMENTS

| | | | |
|---|---|---|---|
| 3,523,138 A * | 8/1970 | Grant ................... 568/816 |
| 4,048,203 A | 9/1977 | Philip |
| 5,308,759 A * | 5/1994 | Gierhart ................ 435/67 |
| 5,382,714 A | 1/1995 | Khachik |
| 5,648,564 A | 7/1997 | Ausich |
| 5,876,782 A | 3/1999 | Sas et al. |
| 5,962,756 A | 10/1999 | Koch et al. |
| 6,191,293 B1 | 2/2001 | Levy |
| 6,221,417 B1 | 4/2001 | Sas et al. |
| 6,262,284 B1 | 7/2001 | Khachik |
| 6,313,169 B1 | 11/2001 | Bowen et al. |
| 6,329,557 B1 | 12/2001 | Rodriguez et al. |
| 6,380,442 B1 | 4/2002 | Madhavi et al. |
| 6,504,067 B1 | 1/2003 | Montoya-Olvera |
| 6,743,953 B1 | 6/2004 | Kumar et al. |
| 6,811,801 B1 * | 11/2004 | Nguyen et al. ............ 426/250 |
| 6,911,564 B1 * | 6/2005 | Khachik ................... 568/816 |
| 2003/0229239 A1 * | 12/2003 | Cordona et al. ........... 554/229 |

OTHER PUBLICATIONS

Arun B. Barua and James Olsen, Xanthophyll Epoxides, Unlike B-Carotene Monoepoxides, are not Detectibly Absorbed by Humans, (2001) pp. 3212-3215.

* cited by examiner

*Primary Examiner*—Christopher R. Tate
(74) *Attorney, Agent, or Firm*—Kevin P. Crosby, Esq.; Daniel C. Crilly, Esq.; Brinkley, Morgan et al.

(57) ABSTRACT

Description of a process to extract, saponify and purify lutein and zeaxantine contained in Marigold flowers free from any genetic manipulation, which have been harvested by hand and dried upon weather so that it neither contains epoxicarotenoids or cis-carotenoids. Fatty acids are removed as its metallic salts and carotenoids are recovered using a polar solvent.

23 Claims, No Drawings

PROCESS FOR THE PURIFICATION OF MARIGOLD XANTHOPHYLLS

BACKGROUND OF THE INVENTION

Carotenoids are one of the groups of pigments most widely distributed in nature and they also have a variety of roles. Some of the main and best known among these are related to its critical role in the photokinetic response of plants, in phototropic response of fish and as of Vitamin A precursors in some mammals and birds.

Among the different types of known carotenoids are those that are oxygenated and are called xanthophylls as a group. Within this particular group are lutein [(3R,3'R,6'R)-β,ε-carotene-3,3'-diol] and zeaxantine [(3R,3'R)-β,β-carotene-3,3'-diol] Frequently, these pigments are found together and with a good degree of concentration in some plants like the Marigold (*Tagetes erecta* sp.) which has found in Peru suitable climatic and soil conditions to produce high quality and completely natural and organic flowers. Traditionally, marigold xanthophylls have found its main application in the pigmentation of chicken skin and eggs yolks.

Although, currently both lutein and zeaxantine have found an important and increasingly growing use as antioxidant and inmunostimulant for some species of animals as well as for human beings. Thus, their beneficial effects have been shown in the treatment of macular degeneration associated with age, various kinds of cancer and cardiovascular diseases, among others. Different mechanisms have been suggested to try to explain how carotenoids protect biological systems, among them the deactivation of electronically reactive species like singlet oxygen and the deactivation of chemically reactive species like peroxyl or alkoxyl radicals that are at times found in cells and thus start dangerous oxidation reactions.

Frequently, commercially available extracts of marigold contain other compounds in addition to the above-mentioned xanthophylls. For example, 1–3% of β-criptoxantine, 2–5% of β-carotene, and variable quantities of epoxide derivatives both lutein and zeaxantine. More often these can constitute from 5% to 20% of xanthophylls of the extract.

Epoxicarotenoids are widely distributed in nature and constitute the most part of carotenoids that human beings consume as part of their fruit and vegetable diets. In fact, epoxides like neoxantine, violaxantine (5,6,5',6'-diepoxi-zeaxantine) and taraxantine (5,6-epoxi-lutein) are more plentiful than 5,6-epoxi-β-carotene.

More recently, it has been shown that some of these epoxides are not efficiently absorbed by humans (Barua, 2001).

Lutein and zeaxantine are naturally found as mono- and di-esters, mainly linked to fatty acids like palmitic, stearic, miristic, etc.

Other components of these extracts are various free fatty acids, waxes, phospholipids, gums, etc. An appropriate method for obtaining lutein and zeaxantine for human consumption should efficiently remove any component other than xanthophylls of interest.

Various processes for such end have been reported for many years. For example, Phillip (1977) obtained lutein esters directly purified from Marigold oleoresins, precipitating them with alcohol and further filtration. Khachik (1995) obtained free lutein crystals from saponified marigold and recrystallizing many halogenated solvents, alcohols, etc. Ausich (1997) recovered lutein by saponifying marigold oleoresins in propilenglicol and centrifugating the material obtained. Koch (1999) treated enzymatically chromoplasts containing carotenoids and then removed insolubles. The sediment obtained is alkalinized in alcohol to finally obtain a concentrate of carotenoids. Levy (2001) prepared a concentrate of lutein trans-esters by first treating marigold oleoresins with a hydrocarbon to obtain esters and then with alcohol to remove what he calls xanthophylls cis-esters. Khachik (2001) reported the method for obtaining lutein concentrates from marigold, by recrystallizing in THF and then washing it with alcohol. Rodriguez et al. (2001) described a method to remove chlorophyls and fats from mechanically reaped extracts of marigold to recover free lutein concentrates. Madhavi (2002) offered a procedure to obtain marigold carotenoides in high concentrations when oleoresins saponify in isopropanol and alkali to centrifuge the mixture obtained and recover lutein crystals.

In all cases, the quality of raw material seems irrelevant in the purification processes. However, concentrates obtained to date by different companies and in accordance with the studies reviewed, do not show a total absence of epoxicarotenoids or arbitrarily omit their presence because these components do not provide the benefits of lutein or zeaxantine and they are commercially obvious.

Agricola Barranca, S.A uses marigold petals of the highest quality coming from cultivation and processes that ensured the absence of theses components and others that could be harmful or of dubious utility for humans. This and the technology described here are used to remove completely those compounds other than lutein and zeaxantine that may be present in saponified marigold extracts.

SUMMARY OF THE INVENTION

The invention described here provides a new process to prepare high purity lutein concentrates of f from marigold petals. This method's main objective is to obtain xanthophylls of a quality suitable to human consumption. The flowers used are of natural selection and have not been genetically manipulated.

Likewise, cultivations are free from pesticides and under absolutely organic conditions. This method guarantees a product free from potentially toxic materials.

The process uses saponified oleoresins obtained from the flowers described above and previously dried at ambient temperature between 30° C. and 35° C., to avoid intensive oxidation and the appearance of critical quantities of epoxized derivatives of lutein and zeaxantine.

Saponification is conventionally carried out using aqueous solutions of KOH or NaOH, mixed with oleoresin at temperatures between 80° C. and 120° for one or two hours to obtain a total hydrolysis.

The saponified product is diluted with enough water to obtain 1 to 15 g of carotenoids per kilogram of dispersion. Normally, this operation is carried out between 30° C. and 50° C. at atmospheric pressure until a completely homogenous dilution is obtained.

In order to remove fatty acids delivered during saponification, the dilution pH of the saponified product is adjusted with aqueous solutions of metallic halogenides such as calcium chloride, zinc chloride, magnesium chloride, etc. This reaction is at 35° C.–50° C. until precipitation of salts from fatty acids is completed. Later, the mixture containing the precipitate is filtered to remove the most quantity of liquid possible and then the residual cake is washed with a polar solvent like alcohol or acetone to find pigments in this phase.

Finally, the solvent is recovered and the obtained residue is a solid with a concentration of xanthophylls between 700 and 900 g per kilogram of product and of which 95% is translutein and 5% is, epoxicarotenoid-free trans-zeaxantine.

DETAILED DESCRIPTION OF THE INVENTION

Marigold is cultivated in Peru avoiding the use of pesticides and promoting absolutely organic techniques throughout the cycle. The seeds used are completely natural, selecting only those from the best plants for yield of carotenoids per kilogram of flower. This is hand harvested only, obtaining inflorescence (petals) which ensures the preparation of high quality flours in which will produce extracts with a high concentration of carotenoids, approximately between 300 and 400 g of xanthophylls per kilogram final of oleoresin, they are practically free of chlorophyll and other components from the green parts of the flower normally used by various companies in this field.

Petals reaped are ensiled for three weeks under environmental conditions and using aqueous solutions certain enzymes to spread some carbohydrates, phospholipids, waxes, proteins and other polymeric materials which are part of the petals but would eventually make the extraction of pigments difficult. Among the selected enzymes are various proteases, pectinases, cellulases, lipases and others that are commercially available. Throughout ensiling liquors rich in sugars are dripped and also other products of enzymatic hydrolysis providing a more enriched substratum even in the pigments.

Later this material is compressed to remove the most quantity of liquid possible and the solid obtained is dried at room temperature, normally between 30 and 35° C. When marigold petals are submitted to the treatment described the formation of epoxicarotenoids is minimum and thus the product is different and of higher quality than if those where the flower has been conventionally dried, for example, in rotary air dryers at 250–280° C.

Dried marigold flour is submitted to a conventional extractive process using no polar or low polarity solvents such as certain hydrocarbons of the hexane type or halo by-products such as methylene chloride. This process normally produces oleoresins containing more than 300 g of pigments per kilogram of product. Then oleoresin is saponified by normal methods, reaching with an alkali like NaOH or KOH in an aqueous solution over several hours at temperatures of 80° C. and 120° C.

The product obtained contains free xanthophylls and a great deal of fats as salts of sodium or potassium reacting in the aqueous medium as tensoactives maintaining the pigments in emulsion. This mixture is adjusted with water to contain between 1 and 15 g of xanthophylls per kilogram of dispersion while the temperature is maintained between 20 and 50° C., preferably at 40° C.

Then a solution of metallic halogenide of formula X-M+ is added slowly, maintaining a vigorous agitation, to carry out the precipitation of fatty acids in the form of their heavier metal salts such as Ca, Mg, Cu, Zn, or their mixtures and preferably as calcium or zinc salts to obtain higher commercial values, as in the case of calcium pannitate, zinc stearate, calcium miristate, etc. The precipitation is complete when the mixture's pH is between 1 and 6, preferably between 4 and 5.

The solid residue obtained is filtered to remove the salt solution and after this operation is completed the cake is washed over the filter with a polar solvent chosen among methanol, ethanol, isopropanol or other similar solvents or mixtures thereof The filtered liquid contains pigments, which are retained in the residual cake as fatty material and other protein residue, waxes, etc. The recovered solids are processed by recovering fatty acids or salts and the filtered liquid evaporates to recover the solvent, obtaining a residue containing between 700 g and 900 g of pigments per kilogram of concentrate from which 90 and 95% is trans-lutein and 5–10% is trans-zeaxantine. The purity of the xanthophylls concentrate so prepared make it especially appropriate for human consumption, whether used a colorant in food manufacture of or as an active ingredient in various pharmacological preparations because of its antioxidant and inmunostimulant properties.

The following are examples, without limitation to the method to be used, to illustrate the preferred conditions under which the described process can be carried out:

EXAMPLE 1

500 g of saponified marigold oleoresin containing about 150 g of xanthophylls per kilogram of substratum are dissolved in 10 liters of water and dispersed until a uniform mixture, free of lumps, is obtained maintaining the temperature at 50° C. and moderate agitation in a reactor at atmospheric pressure. Then an aqueous solution of calcium chloride is slowly added at 5% until the dispersed solid is totally precipitated and the mixture's pH is between 4 and 5. Filter until as much humidity as possible is eliminated. Wash the cake obtained in the filter with acetone at room temperature until the filtrate run clear. Combine the washes and evaporate to recover solvent. The final residue contains 137 g of xanthophylls of which 94% is lutein and 6% is zeaxantine. This concentrate is essentially free of epoxicarotenoids.

EXAMPLE 2

100 g of a saponified marigold oleoresin containing approximately 30 g of carotenoides are dissolved in 5 liters of water and the mixture temperature is adjusted to 40° C. Then a 10% aqueous solution of zinc chloride is slowly added until a final pH of 6.0 is obtained. The neat mixture is filtered, discarding the filtered liquid. The recovered cake is washed with parts of a 1% of zinc chloride solution in acetone until wash runs clear.

All washes are combined and the solvent is recovered by evaporation under vacuum. At the end, a concentrate containing 28 g of carotenoids is obtained of which 93% is lutein and 7% is zeaxantine. The concentration of residue obtained is 900 g of xanthophylls per kilogram.

EXAMPLE 3

250 g of a saponified oleoresin with a concentration of 160 g of xanthophylls per kilogram that contain 40 g of carotenoides are dissolved in 3 liters of acidified water at a pH of 4.0 using phosphoric acid and then mixed at a temperature of 50° C. until a homogenous dispersion is obtained. It is then neutralized with an aqueous 5% magnesium chloride solution at or until a pH between 5 and 6 is obtained. Later the material obtained is filtered discarding the liquid and maintaining the cake. This cake is washed with portions of ethanol at room temperature until the wash is colorless.

After recovering the alcohol we have a solid residue containing about 38 g of xanthophylls of which 94% is lutein and 16% is zeaxantine.

EXAMPLE 4

10 kg of marigold petals manually reaped and coming from pesticide free cultivations and using seeds not genetically manipulated, are dried at room temperature, about 35° C. The flour obtained is extracted the normal way with hexane resulting in 300 g of oleoresin containing about 80 g of xanthophylls, made of lutein and zeaxantine esters. To this extract are added 150 g of a 50% KOH solution and 50 g of propilenglicol. The mixture is heated to 110° C. for an hour under moderated agitation to obtain a completely saponified product. This material is dissolved in 8 liters of water and the mixture temperature is adjusted to 50° C. When dispersion is completely homogenous, the dispersion pH is reduced to 4.0 using a 5% aqueous calcium chloride solution Thus an abundant precipitate is formed, containing mainly calcium salts from fatty acids and it is filtered to remove as much liquid as possible. Then the resulting cake is washed with portions of a 1% solution of calcium chloride in acetone at room temperature until the liquid runs clear.

The solvent is recovered the final residue contains 76 g of xanthophylls of which 95% is lutein and 5% is zeaxantine.

EXAMPLE 5

10 g of flower petals with the same characteristics mentioned in the example above are added to the same quantity of a protease, a cellulase, a lipase, and a pectinase to complete 10 g of enzymes dissolved in 100 g of water at 30° C. The resulting flour is extracted as described in example 4 to obtain 250 g of a oleoresin containing 95 g of carotenoids. To this extract, 100 g of a 50% aqueous KOH solution is added and 30 g of propilenglicol. The saponification is carried out at 110° C. for two hours. The remaining process was carried out similarly as described in example 4 obtaining at the end a concentrate with 90 g of carotenoids of which 93% is trans-lutein and 7% is trans-zeaxantine.

What is claimed is:

1. A process for obtaining xanthophylls from marigold petals, the process comprising:
   drying harvested marigold petals at a predetermined temperature range for a predetermined time period to produce dried petals;
   saponifying the dried petals to obtain saponified extracts;
   dissolving the saponified extracts in water to produce a mixture including emulsions containing from 1 to 20 grams of carotenoids per kilogram of the mixture;
   adding at least one metallic halide to the mixture to adjust a pH of the mixture such that the pH is between about 1 and about 6;
   filtering the pH-adjusted mixture to remove substantially all liquid from the mixture to produce a resultant solid; and
   washing the resultant solid with a polar solvent to recover desired xanthophylls.

2. The process of claim 1, further comprising:
   harvesting marigold petals from marigold flowers that are free of any genetic manipulations to produce the harvested marigold petals.

3. The process of claim 2, wherein the marigold flowers have been cultivated without using a pesticide.

4. The process of claim 1, wherein the step of drying harvested marigold petals comprises:
   drying harvested marigold petals at a temperature range between about 20° C. and about 45° C.

5. The process of claim 1, wherein the step of drying harvested marigold petals comprises:
   drying harvested marigold petals for a time period of about one week to about four weeks under predetermined environmental conditions.

6. The process of claim 1, further comprising:
   adding a solution containing 0.005 to 0.100% by weight of hydrolytic enzymes to the harvested marigold petals prior to the step of drying.

7. The process of claim 6, wherein the hydrolytic enzymes include at least one of cellulase, pectinase, lipase, and protease.

8. The process of claim 1, wherein the polar solvent comprises at least one of saturated hydrocarbon of short chain C5–C8, halogenated hydrocarbon, pentane, hexane, heptane, and octane.

9. The process of claim 1, wherein the polar solvent comprises at least one of methylene chloride, chloroform, carbon tetrachloride, and dichloroethylene.

10. The process of claim 1, wherein the step of dissolving comprises:
    dissolving the saponified extracts in water to produce a mixture including emulsions containing from 5 to 15 grams of xanthophylls.

11. The process of claim 1, wherein fatty acids of the mixture react with the metallic halide.

12. The process of claim 1, wherein the metallic halide comprises at least one of calcium chloride, magnesium chloride, and zinc chloride.

13. The process of claim 1, wherein the step of adding at least one metallic halide to the mixture comprises adding at least one metallic halide to the mixture to adjust a pH of the mixture such that the pH is between about 3 and about 5.

14. The process of claim 1, wherein the polar solvent comprises an alcohol.

15. The process of claim 1, wherein the polar solvent comprises an acetone.

16. The process of claim 1, wherein the step of washing the resultant solid comprises:
    washing the resultant solid at a temperature between about 20° C. and about 45° C.

17. The process of claim 1, wherein the step of saponifying the dried petals comprises:
    saponifying the dried petals to obtain saponified extracts such that the saponified extracts are free of epoxicarotenoids.

18. The process of claim 1, wherein the step of washing the resultant solid comprises:
    washing the resultant solid with a polar solvent to produce desired xanthophylls that are substantially free of cis-carotenoids.

19. The process of claim 1, wherein the step of washing the resultant solid comprises:
    washing the resultant solid with a polar solvent to produce desired xanthophylls that are substantially free of epoxicarotenoids.

20. The process of claim 1, wherein the saponified extracts contain from about 80 to about 250 grams of carotenoids per kilogram of which about 90% to about 95% of the carotenoids is lutein and of which about 5% to about 10% of the carotenoids is zeaxanthin.

21. The process of claim 1, wherein the step of washing the resultant solid comprises:
    washing the resultant solid with a polar solvent to produce a concentrate of xanthophylls containing about 900 grams of xanthophylls per kilogram of which about 95% is lutein and about 5% is zeaxanthin.

22. The process of claim 1, wherein the desired pigments comprise a concentrated product of lutein and zeaxanthin that is appropriate for human consumption.

23. The process of claim 1, further comprising:
    evaporating the polar solvent to produce a concentrate of lutein and zeaxanthin that is free of the polar solvent.

* * * * *